(12) United States Patent
Katayose

(10) Patent No.: US 8,685,655 B2
(45) Date of Patent: Apr. 1, 2014

(54) DISSOCIATION METHOD AND DISSOCIATION AGENT FOR AVIDIN AND BIOTIN DERIVATIVES

(75) Inventor: Satoshi Katayose, Tokyo (JP)

(73) Assignee: JSR Corporation, Tokyo (JP)

( * ) Notice: Subject to any disclaimer, the term of this patent is extended or adjusted under 35 U.S.C. 154(b) by 0 days.

(21) Appl. No.: 13/394,563

(22) PCT Filed: Sep. 16, 2010

(86) PCT No.: PCT/JP2010/066005
§ 371 (c)(1),
(2), (4) Date: Mar. 7, 2012

(87) PCT Pub. No.: WO2011/034115
PCT Pub. Date: Mar. 24, 2011

(65) Prior Publication Data
US 2012/0171763 A1  Jul. 5, 2012

(30) Foreign Application Priority Data
Sep. 17, 2009 (JP) ................................ 2009-215732

(51) Int. Cl.
*G01N 33/53* (2006.01)
*G01N 33/82* (2006.01)
*G01N 33/531* (2006.01)
*G01N 33/566* (2006.01)
*C12Q 3/00* (2006.01)

(52) U.S. Cl.
USPC ................. 435/7.1; 436/501; 436/518; 435/4

(58) Field of Classification Search
None
See application file for complete search history.

(56) References Cited

U.S. PATENT DOCUMENTS

| 6,312,916 B1 | 11/2001 | Kopetzki et al. |
| 6,391,571 B1 | 5/2002 | Kopetzki et al. |
| 6,417,331 B1 | 7/2002 | Kopetzki et al. |
| 2004/0082012 A1 | 4/2004 | Busch et al. |
| 2005/0010028 A1 | 1/2005 | Yanagawa et al. |
| 2005/0208598 A1* | 9/2005 | Cox et al. ...................... 435/7.5 |
| 2008/0138842 A1 | 6/2008 | Boehringer et al. |
| 2008/0255004 A1* | 10/2008 | Neurauter et al. ............. 506/32 |

FOREIGN PATENT DOCUMENTS

| EP | 1016865 | * | 7/2000 | ............ G01N 33/50 |
| JP | 2 184677 | | 7/1990 | |
| JP | 10 28589 | | 2/1998 | |
| JP | 2000 510702 | | 8/2000 | |
| JP | 2004 525354 | | 8/2004 | |
| JP | 2005 507997 | | 3/2005 | |
| JP | 2010 512537 | | 4/2010 | |
| WO | 02 46395 | | 6/2002 | |
| WO | WO 2008/140573 | | 11/2008 | |

OTHER PUBLICATIONS

Hansen et al., (Clin. Chem 1989; 35/8, 1721-1722.).*
Bioquest Technical Note 2008, retrieved from http://aatbio.com/protocol/B1100d1.pdf.*
Previte, M.J.R., et al., "Microwave Triggered Metal Enhanced Chemiluminescence: Quantitative Protein Determination," Analytical Chemistry, vol. 78, No. 23, pp. 8020-8027, (Nov. 3, 2006).
Muratsugu, M., et al., "Comparison of the Solid Phase-supported Receptor and Ligand Competitive Assays for Biotin," Journal of Health Science, vol. 55, No. 6, pp. 939-945, (Dec. 2009).
Hirsch, J.D., et al., "Easily reversible desthiobiotin binding to streptavidin, avidin, and other biotin-binding proteins: uses for protein labeling, detection, and isolation," Analytical Biochemistry, vol. 308, No. 2, pp. 343-357, (2002).
Hu, B., et al., "Method for Screening and MALDI-TOF MS Sequencing of Encoded Combinatorial Libraries," Analytical Chemistry, vol. 79, No. 19, pp. 7275-7285, (Aug. 23, 2007).
International Search Report Issued Oct. 12, 2010 in PCT/JP10/66005 Filed Sep. 16, 2010.
Wu Zheng-ming, et al., "A fluorescent enzyme immunoassay based on cyclic accumulation of horseradish peroxidase", Chemical Sensors, vol. 27, No. 4, Dec. 31, 2007, pp. 43-47 with English abstract.
European Search Report in application No. 10817228.9, dated Feb. 6, 2014.
M. Xiong, et al., "Biotin-triggered release of poly(ethylene glycol)-avidin from biotinylated polyethylenimine enhances in vitro gene expression", Bioconjugate Chemistry, vol. 18, No. 3, Mar. 22, 2007, pp. 746-753.
J. Morris, et al., "Affinity precipitation of proteins by polyligands", Biotechnology and Bioengineering, vol. 41, Jan. 1, 1993, pp. 991-997.

* cited by examiner

*Primary Examiner* — Jacob Cheu
*Assistant Examiner* — Carmencita M Belei
(74) *Attorney, Agent, or Firm* — Oblon, Spivak, McClelland, Maier & Neustadt, L.L.P.

(57) ABSTRACT

A method for dissociating avidin or streptavidin efficiently from a biotin derivative, thereby making it possible to isolate a target material efficiently under a mild condition in a short period, and a dissociation agent for use thereof, are provided. The method for dissociating avidin or streptavidin from a biotin derivative, includes mixing a combination of avidin or streptavidin with desthiobiotin with a water-soluble polymer to which biotin or a derivative thereof is bound.

15 Claims, 1 Drawing Sheet

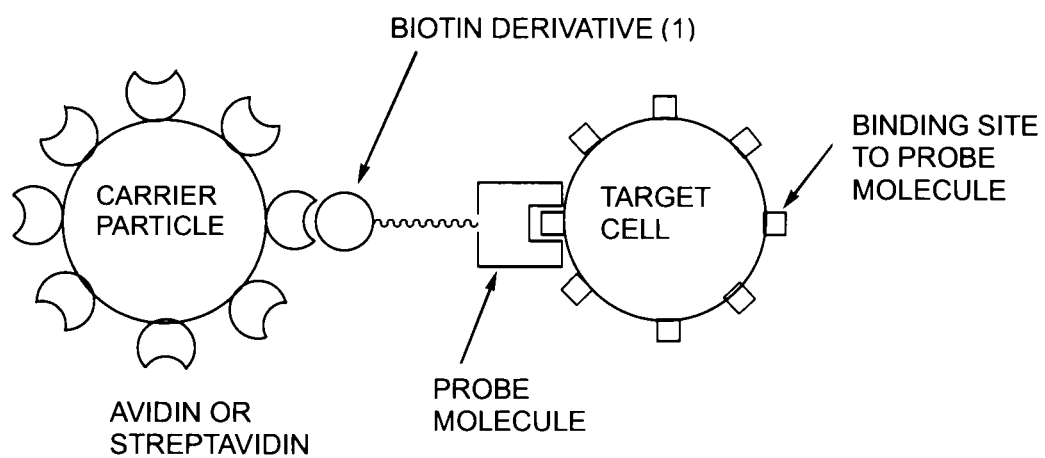

DISSOCIATION METHOD AND DISSOCIATION AGENT FOR AVIDIN AND BIOTIN DERIVATIVES

FIELD OF THE INVENTION

The present invention relates to a method for dissociating avidin or streptavidin from a biotin derivative, and a dissociation agent for use in the method.

BACKGROUND OF THE INVENTION

Avidin or streptavidin (hereinafter referred to as (strept) avidin) has highly specific affinity with biotin or any derivatives thereof. When the both are mixed with each other under a physiological condition, they are easily bound to form a complex (the complex between (strept)avidin and biotin or between (strept)avidin and the biotin derivative are generally called as "ABC complex"). This property is utilized for isolation of a target substance or a target material such as cells (Patent Literature 1).

A carrier for capturing a target substance may be prepared and the target substance may be captured by use of this carrier, for example, a biotin-labeled probe molecule (such as an antibody having binding affinity for the target substance), to which biotin is beforehand bound, are mixed with an insoluble carrier to which (strept)avidin is immobilized under a physiological condition, to form an ABC complex. Thereafter, if the ABC complex or the binding between the probe molecule and the target substance can be cleaved, the target substance can be isolated (Patent Literature 1).

However, the affinity of (strept)avidin for biotin is so strong that it is very difficult to cleave the ABC complex under physiological condition. In order to dissociate (strept)avidin from a biotin derivative, a severe condition, for examples, a condition wherein the combination is treated with a guanidine hydrochloride salt in pH of about 1.5, and a condition wherein the combination is boiled in a buffer solution for SDS polyacrylamide gel electrophoresis to which a reducing agent is added, is required. Accordingly, when a target to be isolated is a protein, cells, or other target substance that is easily damaged by a severe pH, heat or salt concentration, or physical shear force, it is generally difficult to isolate the target substance wherein the physiological activity thereof is maintained.

Therefore, methods for easily isolating a target substance, for example, a method using a biotin derivative which binds to (strept)avidin with lower affinity than biotin (Patent Literature 2); and a method using an avidin variant lower in affinity with biotin than avidin (Patent Literature 3), are proposed. For example, a method in which, instead of biotin, desthiobiotin or some other biotin derivative which binds to (strept) avidin with lower affinity than biotin (Patent Literature 2) is used to prepare a capturing carrier as described above, a target substance is captured thereby, and then a large amount of biotin is added thereto for cleaving the ABC complex to isolate the target substance. In this case, the biotin is thought to function as a competitive inhibitor for bonding between desthiobiotin and (strept)avidin. However, according to this method in which biotin is used as competitive inhibitor, it would be difficult to efficiently cleave the ABC complex. Thus, the target substance would be difficult to be efficiently isolated.

PRIOR ART DOCUMENTS

Patent Document

Patent Document 1: JP-A-2010-512537
Patent Document 2: JP-A-H02-184677
Patent Document 3: JP-A-H10-028589

SUMMARY OF THE INVENTION

Problem to be Solved

The present invention provides a method for dissociating (strept) avidin efficiently from a biotin derivative with lower affinity than biotin, as mentioned above, under a mild condition in a short period, and a dissociation agent for use in the method.

Means for Solving the Problem

The inventor has made various investigations to find out a means for dissociating (strept)avidin efficiently from a biotin derivative with lower affinity than biotin, as mentioned above. As a result, the inventor has unexpectedly found out that by use of a water-soluble polymer to which biotin or the like is bound as a dissociation agent, (strept)avidin is efficiently dissociated from the biotin derivative with lower affinity than biotin under a mild condition. Thus, the invention has been provided.

Thus, the invention provides a method for dissociating avidin or streptavidin from a biotin derivative (1) which binds to avidin with lower affinity than biotin, comprising the step of mixing a combination of avidin with the biotin derivative (1), or a combination of streptavidin with the biotin derivative (1) (hereinafter the combination being referred to as "avidin-biotin complex") with a water-soluble polymer to which biotin or a derivative (2) thereof is bound (hereinafter the polymer being referred to as "dissociation agent").

The invention also provides a method for isolating a target substance, comprising:

(a) the step of mixing a capturing carrier with the target substance in an aqueous solvent to obtain a liquid mixture 1, (b) the step of mixing the liquid mixture 1 with a water-soluble polymer to which biotin or a derivative (2) thereof is bound to obtain a liquid mixture 2, and (c) the step of isolating the target substance from the liquid mixture 2, wherein the capturing carrier is a combination of the following (A) and (B):

(A) avidin or streptavidin immobilized to an insoluble carrier, and (B) a biotin derivative (1) which is immobilized to a substance having a specific affinity for the target substance (hereinafter the specific affinity substance being referred to as "probe molecules"), and binds to avidin with lower affinity than biotin.

Furthermore, the invention provides a dissociation agent which is used for dissociating avidin or streptavidin from a biotin derivative (1), and contains a water-soluble polymer to which biotin or a derivative (2) thereof is bound.

Effects of the Invention

According to the method of the invention, the complex between (strept)avidin and the biotin derivative (1) can be efficiently cleaved under a mild condition in a short period to dissociate (strept)avidin and the biotin derivative (1) from each other.

When this method is applied to the isolation of a target substance, the obtained target substance bound to the capturing carrier can easily be isolated. Even when the target substance is a substance with lower stability against temperature condition, pH condition or some other condition, such as a protein or one or more cells, the use of the invention makes it possible to isolate the target substance in which the activity thereof is maintained.

BRIEF DESCRIPTION OF DRAWINGS

FIG. 1 is a diagram illustrating that a capturing carrier used in an embodiment of the invention is bound to a target cell.

DETAILED DESCRIPTION OF THE INVENTION

Hereinafter, specific embodiments of the invention; the method for dissociating (strept)avidin from a biotin derivative (1), and the dissociation agent for use in the method, are described.

(Method for Dissociating (strept)avidin from a Biotin Derivative)

The method according to the embodiment of the invention for dissociating (strept)avidin from a biotin derivative (1) comprises the step of mixing an avidin-biotin complex with a water-soluble polymer to which biotin or a derivative (2) thereof is bound. Usually, the dissociating method of the invention is carried out in a solvent comprising, mainly, water. In this case, the avidin-biotin complex exists in the solvent as dissolved form. However, in the case where, for example, the avidin-biotin complex is bound to an insoluble carrier, the avidin-biotin complex may be dispersed, together with the carrier, into the solvent.

(Avidin-Biotin Complex)

The avidin-biotin complex used in the invention is a combination of avidin or streptavidin with a biotin derivative (3) which binds to avidin with lower affinity than biotin (biotin is a compound represented by the below formula (3)). Avidin or streptavidin used herein may be a commercially available product. They may be a compound isolated from the nature world and then purified, or a compound produced artificially by genetic engineering technique, or an avidin or streptavidin derivative that is modified or varied within the degree that the binding capacity thereof to biotin is not lost. Examples of the avidin or streptavidin derivative include chemically modified (for example, succinylated) avidin or streptavidin subjected, and an avidin or streptavidin monomer (that is, the avidin or streptavidin usually forms a tetramer thereof).

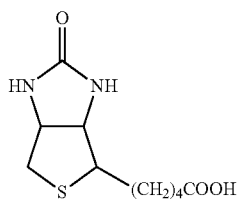

(3)

The biotin derivative (1) is not particularly limited as far as the derivative is a biotin derivative which binds to avidin with lower affinity than biotin. According to the lower binding affinity to avidin of the biotin derivative (1) than biotin, when the avidin-biotin complex thereof is mixed with a water-soluble polymer to which biotin or a derivative (2) thereof is bound, (strept)avidin and the biotin derivative (1) are effectively dissociated from each other.

Examples of the biotin derivative (1) include derivatives having a cyclic moiety of biotin different from that of biotin, such as desthiobiotin (a compound represented by the following formula (4)), 2-iminobiotin (a compound represented by the following formula (5)) and 3,4-diaminobiotin (a compound represented by the following formula (6)) and chemically modified products of these compounds:

[Chemical formula 2]

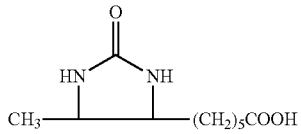

(4)

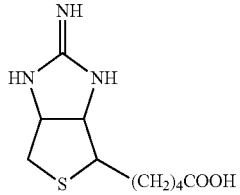

(5)

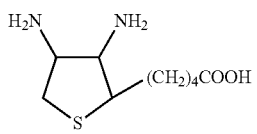

(6)

The phrase "(any compound) lower binding affinity with avidin than biotin" means that the binding constant thereof (with avidin) is one order or less smaller than that of biotin with avidin ($10^{15}$ M). The binding constant with avidin of each of the compounds represented by the formulae (4) to (6), respectively, is from $10^6$ to $10^{13}$ M.

(Avidin-Biotin Complex Immobilized to an Insoluble Carrier)

The avidin-biotin complex used in the invention may be immobilized through (strept)avidin to an insoluble carrier. When the avidin-biotin complex is immobilized to the insoluble carrier, the avidin-biotin complex can easily be isolated from a dispersion liquid containing the avidin-biotin complex by centrifugation, filtration or other methods.

The form or shape of the insoluble carrier used for immobilization of (strept)avidin is not particularly limited. Examples of the carrier include organic or inorganic particles, a tabular substrate, a substrate having fine channels, and a micro-well plate. Among the organic particles having an average particle diameter of 0.5 to 10 μm, and being made of one or more organic synthetic polymers, for example, mainly of polystyrene, are preferable. The particles are preferably magnetic particles since the particles can be isolated by magnetism.

Examples of a commercially available product of the magnetic particles include Dynabeads M-450 Tosylactivated (manufactured by Invitrogen (Co.)) and Magnosphere MS300/Carboxyl (manufactured by JSR Corp.). The magnetic particles are preferably produced by a known method (for example, JP-B-H05-010808, or JP-A-2007-288133), and the non-specific adsorption of a protein, cells and others can be decreased.

The method for immobilizing (strept)avidin to the insoluble carrier is not particularly limited, and may be publicly known methods (see, for example, JP-A-2001-158800). In the case of using, for example, an insoluble carrier having carboxyl groups on the surface thereof, (strept)avidin can be immobilized to the insoluble carrier by formation of amide bonds through reaction of amino groups in molecules of (strept)avidin with the carboxyl groups on the carrier surface in the presence of a dehydration condensing agent such as water-soluble carbodiimide. In such a method, the carboxyl groups on the carrier may be reacted with the dehydration condensing agent in advance, and then avidin or streptavidin may be added thereto, to complete the reaction.

(Capturing Carrier)

The avidin-biotin complex used in the invention may be a combination of the following (A) and (B) (hereinafter the combination being referred to as "capturing carrier"):

(A) avidin or streptavidin immobilized to an insoluble carrier, and (B) a biotin derivative (1) which is immobilized to a substance having a specific affinity for a target substance (hereinafter the specific affinity substance being referred to as the "probe molecules").

The species of the probe molecules is not particularly limited, and examples thereof include an antibody against a target substance, proteins such as lectin and enzymes, and saccharides. The probe molecules have a binding property to a target substance specifically, and are bound to the biotin derivative (1). The probe molecules may be bound to the biotin derivative (1) directly or through a spacer.

The biotin derivative (1) immobilized to the probe molecules is a biotin derivative (1) showing lower affinity than that of biotin for avidin, this biotin derivative having been described in the above section regarding the avidin-biotin complex.

The method for bonding the biotin derivative (1) to the probe molecules is not particularly limited, and may be, for example, similar to the above-mentioned method for immobilizing (strept)avidin to the surface of a carrier. In the case of using, for example, probe molecules having amino groups, a carboxyl group in biotin molecule may be reacted with amino groups in the probe molecules, in the presence of a dehydration condensing agent such as water-soluble carbodiimide, thereby amide bond is formed, to obtain biotin-bound probe molecules.

When the isolating carrier is used as the avidin-biotin complex, the avidin-biotin complex is bound specifically to a target substance so that the target substance bound to the capturing carrier can be specifically isolated.

FIG. 1 shows a conceptual view of the capturing carrier bound to the target substance.

(Target Substance)

The target substance is not particularly limited, and examples thereof include cells (for example, various cells of bacteria, eumycetes, animals orplants), viruses, proteins (for example, various antigens, antibodies or enzymes), nucleic acids such as single-stranded or double-stranded DNA or RNA, steroid lipids such as estrogen, glycolipids, and polysaccharides. Specific examples of the cells for the target substance (hereinafter the cells being referred to as "target cells") are not particularly limited, and examples thereof include normal cells (for example, stem cells such as hematopoietic stem cells, blood cells such as white blood cells), cancer cells (for example, circulating cancer cells in peripheral blood, which originate from mammary cancer, lung cancer, or some other, exfoliative cancer cells present in feces, which originate from colon cancer or some other, cancer cells in menstrual blood, which originate from uterine cancer, and cancer cells present in urine, which originate from bladder cancer). The target substance can be efficiently isolated by the method for isolating target substance according to the invention.

(Dissociation Agent)

In the method of the invention for dissociating (strept) avidin from a biotin derivative (1), an avidin-biotin complex is mixed with a water-soluble polymer to which biotin or a derivative (2) thereof is bound (hereinafter the polymer being referred to as "dissociation agent"), to cleave the binding between (strept)avidin and the biotin derivative (1) to dissociate the (strept)avidin from the biotin derivative (1).

The dissociation agent is most preferably a water-soluble polymer to which biotin is bound.

Examples of the biotin derivative (2) that may be used in the dissociation agent include derivatives having the same cyclic moiety as biotin, such as biocytin (biotin-ε-N-lysine: a compound represented by a formula (7) illustrated below), biotin-N-hydroxysuccinic imide ester (a compound represented by a formula (8) illustrated below), and a compound represented by a formula (9) illustrated below (biotinyl-3,6, 9-trioxaundecanediamine); or derivatives each having a cyclic moiety different from that of biotin, these derivatives having been described in the above section regarding the avidin-biotin derivative. Of these compounds, preferred are derivatives having the same cyclic moiety as biotin since the derivatives show high affinity for avidin.

[Chemical formula 3]

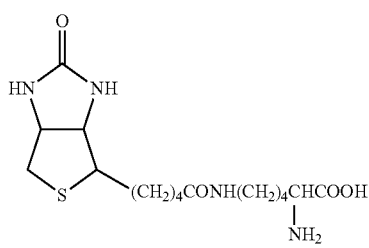

(7)

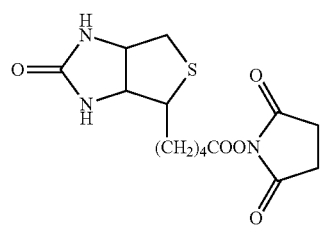

(8)

(9)

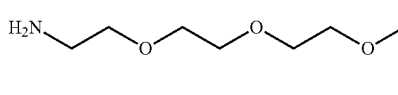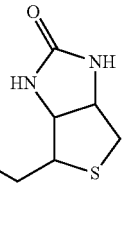

In order to dissociate (strept)avidin from the biotin derivative (1), for example, the dissociation agent may be added to a liquid sample containing an avidin-biotin complex under a physiological condition, and then they are mixed with each other. The physiological condition is preferably the following condition: a temperature of 20 to 40° C., a pressure of about 1 atm., and a pH of 5 to 9.

The (strept)avidin can be dissociated efficiently from the biotin derivative (1) by the use of the dissociation agent of the subject invention. By addition of the dissociation agent to an aqueous sample which contains an avidin-biotin complex, avidin or the derivative (2) thereof contained in the dissociation agent competes with the biotin derivative (1) bound to (strept)avidin, to dissociate (strept)avidin from the biotin derivative (1). Further, the dissociation agent, in which the biotin or the derivative (2) thereof is bound to the water-soluble polymer, can dissociate (strept)avidin more efficiently from the biotin derivative (1) than using free biotin or the derivative (2) thereof which is not bound to any water-soluble polymer or the like, although the reason is not clear.

The water-soluble polymer is not particularly limited as far as the polymer is a water-soluble polymer and can be bound to biotin or the derivative (2) thereof. The polymer is preferably a water-soluble polymer having an amino group, a sulfhydryl group, a carboxyl group, or some other functional group because the water-soluble polymer can be bound to biotin through a carboxyl group in the biotin molecule. Examples thereof include water-soluble proteins, polysaccharides, and organic synthetic polymers having reactive functional groups such as amino group. Preferred examples of the water-soluble proteins include BSA (bovine serum albumin), and HAS (human serum albumin). Examples of the polysaccharides include CMC (carboxylmethylcellulose), and chitosan. Examples of the organic synthetic polymers having a reactive functional group include PAA (polyacrylic acid), polyallylamine, and other synthetic polymers; and polyamino acids such as polylysine, polyaspartic acid.

In the invention, the word "water-soluble" means a property that a substance can be dissolved in solvent to give a 1 mg/mL solution without generation of white turbidness.

The molecular weight of the biotin-bound water-soluble polymer is not particularly limited, and is preferably from 1,000 to 1,000,000. When the molecular weight of the biotin-bound water-soluble polymer is within this range, the avidin-biotin complex can be efficiently dissociated. The molecular weight of the biotin-bound water-soluble polymer may be measured by, for example, gel permeation chromatography.

The average molecular number of the biotin or the derivative (2) thereof bound to individual molecules of the water-soluble polymer is preferably as large as possible as far as the water-solubility is not lost. The average number is preferably from 2 to 2,000, more preferably from 5 to 1,000, even more preferably from 10 to 100. The larger the molecular number of the biotin or the derivative (2) thereof bound to the water-soluble polymer per the polymer is, the more efficient the dissociation of (strept)avidin and the biotin derivative (1) is. The average molecular number of the biotin or the derivative (2) thereof bound to individual molecules of the water-soluble polymer may be measured by a method described in Examples described below (HABA method).

The method for binding the biotin or the derivative (2) thereof to the water-soluble polymer is, for example, a method of reaction of biotin or the derivative (2) thereof with a water-soluble polymer having at least one of a carboxyl group and an amino group. When the water-soluble polymer contains an amino group, the method may be a method of dehydration-condensation of the amino group in the water-soluble polymer with the carboxyl group of biotin. When the water-soluble polymer contains a carboxyl group, the method may be a method of dehydration-condensation of the carboxyl group in the water-soluble polymer with the amino group of the amino-group-having biotin derivative.

(Method for Isolating a Target Substance)

The method of the invention, for isolating a target substance, includes: the step (a) of mixing a capturing carrier with the target substance in an aqueous solvent to obtain a liquid mixture 1, the step (b) of mixing the liquid mixture 1 with a water-soluble polymer to which biotin or a derivative (2) thereof is bound, to obtain a liquid mixture 2, and the step (c) of isolating the target substance from the liquid mixture 2. The capturing carrier is:

a combination of the following (A) and (B):

(A) avidin or streptavidin immobilized to an insoluble carrier, and (B) a biotin derivative (2) which is immobilized to a substance having a specific affinity for the target substance (hereinafter the specific affinity substance being referred to as "probe molecules").

(Step of Mixing a Capturing Carrier with a Target Substance in an Aqueous Solvent, to Obtain a Liquid Mixture 1)

This step is a step of binding a capturing carrier to a target substance. Specifically, a capturing carrier is mixed with a target substance, to bind the probe molecules contained in the capturing carrier specifically to the target substance or to molecules contained in the target substance and having affinity for the probe molecules.

The capturing carrier and the target substance are as described above. The aqueous solvent is preferably a solvent having a pH of 5 to 9 containing water as a major medium, and is more preferably a buffer solution such as a phosphoric acid buffered solution or a Tris buffered solution.

In the case of mixing the capturing carrier with the target substance, it is preferred to mix the capturing carrier dispersed in the aqueous solvent with the target substance dissolved or dispersed in the same or different aqueous solvent. After the mixing, it is preferred to stir the mixture at 10 to 40° C. for 1 to 60 minutes. By the stirring under such a condition, the capturing carrier and the target substance are efficiently bound to each other.

The amount of the mixed capturing carrier may be appropriately adjusted in accordance with the amount of the target substance contained in the sample.

(Step of Mixing the Liquid Mixture 1 with a Water-Soluble Polymer to Which Biotin or a Derivative Thereof is Bound, to Obtain a Liquid Mixture 2)

This step is a step of adding a dissociation agent to cleave the binding between (strept)avidin in the capturing carrier and the biotin derivative (1), for dissociating the (strept)avidin and the biotin derivative (1) from each other. In to the case of mixing the liquid mixture 1 with the dissociation agent, it is preferred to mix a solution in which the dissociation agent is dissolved in an aqueous solvent with the liquid mixture 1. After the mixing, it is preferred to stir the mixture at 10 to 40° C. for 1 to 60 minutes. By the stirring under such a condition, (strept)avidin and the biotin derivative (1) are efficiently dissociated from each other.

This step may include a step of isolating the capturing carrier from the liquid mixture 2. When the capturing carrier contains magnetic particles, the capturing carrier can easily be isolated by use of a magnetic stand.

(Step of Isolating the Target Substance from the Liquid Mixture 2)

The present step is a step of isolating the target substance contained in the liquid mixture 2. Through this step, the target substance is isolated from the insoluble carrier and the like. The step may be carried out by any kinds of method. When the capturing carrier contains magnetic particles, the capturing carrier can easily be isolated by use of a magnetic stand. When the capturing carrier does not contain magnetic particles, the method used in the step may be, for example, a method of centrifugation of the dispersion under such a centrifuge condition in which the target substance does not precipitate, a method of filtration of the dispersion through a filter having a pore diameter in the degree that the target substance is not captured.

EXAMPLES

Hereinafter, the detail embodiments of the subject invention are described by Examples. However, the invention is not restricted by these Examples.

Preparation Example 1

Production of Desthiobiotin-Bound Probe Molecules (Anti-Ep-CAM Antibody)

5 mg of desthiobiotin (manufactured by MP Biomedicals Inc.) was dissolved into 0.5 mL of dimethylsulfoxide. 5.36 mg each of N-hydroxysuccinimide (NHS) and 1-ethyl-3-(3-dimethylaminopropyl)carbodiimide hydrochloride salt (EDC hydrochloride salt) (1.2 equivalents to carboxyl groups on desthiobiotin) were added to this solution, and were subjected to reaction at room temperature for 60 minutes. 3 μL aliquot was sampled from this reaction liquid, and was added to 2 mg of an antibody against Ep-CAM (anti-Ep-CAM antibody: clone Ber-EP4, purchased from Daco International Ltd.), which is an epithelial specific antigen, dissolved in 1 mL of PBS (phosphoric acid buffer saline), and was subjected to reaction at room temperature for 3.5 hours. Unreacted desthiobiotin was removed by ultrafiltration to yield a desthiobiotin-bound anti-Ep-CAM antibody.

Preparation Example 2

Preparation of an Avidin-Biotin Complex (Capturing Carrier)

1 mg of streptavidin magnetic particles (Dynabeads M-280 Streptavidin, manufactured by Invitrogen (Co.)) and 2 μg of the desthiobiotin-bound anti-Ep-CAM antibody yielded in Preparation Example 1 were added into a test tube, and were mixed in PBS for 30 minutes to bind streptavidin to desthiobiotin. Next, a magnetic stand was used to isolate the magnetic particles from the reaction liquid. The reaction liquid was washed with 0.05%-Tween-20-containing PBS 3 times to remove unreacted desthiobiotin-bound probe molecules, to yield an avidin-biotin complex (capturing carrier) in which the desthiobiotin-bound probe molecules were bound to the streptavidin magnetic particles.

Preparation Example 3

Preparation of a Dissociation Agent (1) (Synthesis of Biotin-Bound Bovine Serum Albumin (BSA))

200 mg of biotin (molecular weight: 244.31) was dissolved into 2.76 mL of dimethylsulfoxide, and 173 mg each of NHS and EDC hydrochloride salt (1.1 equivalents to carboxyl groups on biotin) were added, and subjected to reaction at room temperature for 60 minutes. 0.508 mL and 1.27 mL aliquots were sampled from this reaction liquid. Each of the aliquots were added to a solution in which 1 g of BSA (manufactured by Sigma (Co.)) was dissolved in 50 mL of 10-mM phosphoric acid buffer solution (pH: 7.0), and were subjected to reaction at room temperature for 3.5 hours. Unreacted biotin was removed by ultrafiltration to yield water-soluble biotin-bound BSA. Through this process, a dissociation agent in which six (6) in average of biotin were bound to one molecule of BSA (hereinafter referred to as BSA-Biotin 6), and a dissociation agent in which ten (10) in average of biotin were bound to one molecule of BSA (hereinafter referred to as BSA-Biotin 10), were yielded. The quantity of biotin bound to each of BSAs was determined by an HABA method according to Green et al. (4-hydroxyazobenzene-2-carboxylic acid, N. M. Green, Methods in Enzymology, vol. 18, pp. 418-424, 1970).

Preparation Example 4

Preparation of a Dissociation Agent (2) (Synthesis of Biotin-Derivative-Bound Polyacrylic Acid)

0.1 g of polyacrylic acid (PAA, manufactured by Wako Pure Chemical Industries, Ltd., molecular weight of 250,000) was dissolved into 5 mL of a 10-mM phosphoric acid buffer solution (pH: 7.0), and 133 mg of EDC hydrochloride salt (0.5 equivalent to carboxyl groups of polyacrylic acid) was added. Subsequently, 0.835 mL or 1.67 mL of 10 mg/mL solution of the compound represented by the formula (7) (Biotin-PEO-LC-Amine, manufactured by Thermo Fisher Scientific Inc.), which is a biotin derivative having an amino group, dissolved in dimethylsulfoxide, were added, and were subjected to reaction at room temperature for 3.5 hours. Unreacted biotin was removed by ultrafiltration to yield water-soluble biotin-bound PAA. The quantity of biotin bound to PAA was determined according to the HABA method.

Through this process, a dissociation agent in which fifteen (15) in average of biotin derivative were bound to one molecule of PAA (named PAA-Biotin 15) and a dissociation agent in which forty (40) in average of biotin derivative were bound to one molecule of PAA (named PAA-Biotin 40), were yielded.

Preparation Example 5

Preparation of Target Cells

Culture medium was removed from a petri dish in which HT-29 cells (target cells) were cultivated, and 1 mL of 2-mM-EDTA-containing PBS was added thereto. The cells were incubated at 37° C. for 5 minutes to suspend the cells from the petri dish and were isolated by pipetting, and the cells were diluted with PBS to yield a cell-suspension liquid at a concentration of $2.0 \times 10^5$ cells/mL. The HT-29 cell expresses an Ep-CAM antigen.

[Measurement of Number of Cells]

The number of cells was determined by measuring the quantity of genome DNA according to the quantitative PCR method.

(1) Measurement of the Number of Cells Bound to the Capturing Carrier:

50 µL of 0.8 mg/mL solution of proteinase K (protease, manufactured by Qiagen N.V.) dissolved in 10-mM Tris-HCl buffer solution (pH: 8.3) was added to the total amount of the combination of the capturing carrier and the target cells yielded in the below Examples and Comparative Example, and the resultant was reacted by heating at 55° C. for 15 minutes to elute DNA. Subsequently, this solution was heated at 95° C. for 20 minutes to inactivate proteinase K. 20 µL of the resultant DNA solution was added to 30 µL of a quantitative PCR cocktail (Fast Start Taq, manufactured by Roche (Co.)) to carry out quantitative PCR. Other DNA solutions prepared by the same method using predetermined number of cells were used to prepare a calibration curve. A 7500 Real-Time PCR System, manufactured by Applied Biosystems (Co.), was used for the quantitative PCR.

(2) Measurement of the Number of Cells Isolated from the Capturing Carrier:

The measurement was carried out in the same way as the measurement of the number of the cells bound to the capturing carrier, except that 100 µL aliquot of the total 250 µL volume of the cell-suspension liquid obtained by using the dissociation agent of the below Examples or Comparative Example (the dissociation agent was biotin in Comparative Example) were used instead of the total amount of the combination of the capturing carrier and the target cells, in order to measure the number of the cells in the total volume of the cell-suspension liquid after the dissociation.

[Efficiency of Dissociation]

The efficiency of dissociation of (strept) avidin from the biotin derivative was determined according to the following equation:

Efficiency of Dissociation (%)="the number of the cells isolated from the capturing carrier"/"the number of the cells bound to the capturing carrier"×100

Example 1

1 mg aliquots of the capturing carrier yielded in Preparation Example 2 were added into test tubes. 1 mL of PBS containing 0.6% by mass of citric acid and 0.5% by mass of BSA was added to each of the aliquots to yield suspension liquid of capturing carrier. 50 µL of the cell-dispersed liquid yielded in Preparation Example 5 was added to this suspension liquid of capturing carrier, and were mixed at 4° C. for 30 minutes to bind the capturing carrier to the HT-29 cells. Next, a magnetic stand was used to isolate the capturing carrier, and then the carrier was washed with PBS three times to isolate the target cells bound to the capturing carrier from unbound cells and other solute components. The number of the cells bound to the isolated capturing carrier was measured, and the number was 8,500, which was 85% of the number of the cells used for the Example.

250 µL of 0.2% by mass solution of the BSA-Biotin 6 in PBS yielded in Preparation Example 3 was added to the capturing carrier bound to the target cells, and mildly mixed at room temperature for 20 minutes. Thereafter, a magnetic stand was used to isolate the particles, thereby the HT-29 cells dissociated in the supernatant were collected. The cells were observed using an optical microscope. As a result, the form of the cells in the supernatant was maintained.

The efficiency of dissociation of the target cells is shown in Table 1. In Table 1, the item "biotin concentration in dissociation solution" means a value of the percentage by mass of biotin calculated from the concentration of the dissociation agent and the degree of biotinilation of the dissociation agent.

Examples 2 to 4

The dissociation efficiency was obtained in the same way as in Example 1, except that a dissociation agent shown in Table 1 was used instead of the BSA-Biotin 6.

Comparative Example 1

The dissociation efficiency was obtained in the same way as in Example 1, except that a 10 mM solution of biotin in PBS was used instead of the 0.2%-by-mass solution of BSA-Biotin 6 in PBS.

TABLE 1

Dissociation efficiency of streptavidin magnetic particles-desthiobiotin-bound probe molecules-target substance complex

| | Dissociation agent | Dissociation agent concentration | Dissociation agent liquid amount (µL) | Biotin concentration (% by mass) in dissociation solution | Dissociation efficiency (%) |
|---|---|---|---|---|---|
| Example 1 | BSA-Biotin6 | 2.0 mg/ml | 250 | 0.0043 | 70 |
| Example 2 | BSA-Biotin10 | 2.0 mg/ml | 250 | 0.0071 | 96 |
| Example 3 | PAA-Biotin15 | 2.0 mg/ml | 250 | 0.0045 | 75 |
| Example 4 | PAA-Biotin40 | 2.0 mg/ml | 250 | 0.0075 | 95 |
| Comparative Example 1 | Biotin | 10 mM | 250 | 0.24 | 3 |

As shown in Table 1, it was verified that as compared with Comparative Example 1 in which free biotin was used instead of dissociation agent, Examples 1 to 4, in which the biotin-bound water-soluble polymer was used as the dissociation agent, can dissociate (strept)avidin from the biotin derivative with a very high efficiency to isolate the target cells although the biotin concentration in the dissociation solution was very small.

The invention claimed is:

1. A method for dissociating avidin or streptavidin from a complex of (a) avidin or streptavidin and (b) a first biotin derivative, comprising:
   combining (a) avidin or streptavidin immobilized on an insoluble carrier and (b) a first biotin derivative to form a complex, wherein the first biotin derivative has a cyclic moiety different from a cyclic moiety of biotin and binds to avidin or streptavidin with a lower affinity than biotin, having an affinity binding constant to avidin of $10^6$ to $10^{13}$ M; and
   dissociating avidin or streptavidin from the a first biotin derivative with a disassociation agent in a liquid sample under a physiological condition, wherein the disassociation agent comprises biotin covalently bound to a water-soluble polymer or a second biotin derivative covalently bound to the water-soluble polymer, wherein the water-soluble polymer has a density of 5 to 1,000 molecules of the biotin or the second biotin derivative per molecule of the water-soluble polymer,
   wherein the second biotin derivative has the same cyclic moiety as biotin; and
   wherein the dissociation agent can dissociate avidin or streptavidin from the first biotin derivative with a dissociation efficiency of at least 70% and more efficiently than the biotin or the second biotin derivative not bound to the polymer.

2. The method of claim 1, wherein the dissociation agent comprises biotin covalently bound to the water-soluble polymer.

3. The method of claim 1, wherein the first biotin derivative is one or more members selected from the group consisting of desthiobiotin, 2-iminobiotin, and 3,4-diaminobiotin.

4. The method of claim 1, wherein the water-soluble polymer has a molecular weight of from 1,000 to 1,000,000 when measured by gel permeation chromatography.

5. The method of claim 1, wherein the water-soluble polymer has a density of 10 to 100 molecules of the biotin or the second biotin derivative density of biotin per molecule of the water-soluble polymer.

6. The method of claim 1, wherein the water-soluble polymer comprises a water-soluble protein, a water-soluble polysaccharide, or a water-soluble organic synthetic polymer.

7. The method of claim 5, wherein the water-soluble polymer comprises bovine serum albumin, human serum albumin, or both, as a water-soluble protein.

8. The method of claim 6, wherein the water-soluble polymer comprises CMC (carboxylmethylcellulose), chitosan, or both, as a water-soluble polysaccharide.

9. The method of claim 6, wherein the water-soluble polymer comprises an organic synthetic polymer comprising a reactive functional group.

10. The method of claim 9, wherein the organic synthetic polymer comprising a reactive functional group comprises PAA (polyacrylic acid), polyallylamine, polylysine, polyaspartic acid, or a combination thereof.

11. The method of claim 1, wherein the dissociation agent comprises the second biotin derivative covalently bound to the water-soluble polymer.

12. The method of claim 1, wherein the insoluble carrier comprises organic particles, wherein an average diameter of the organic particles is from 0.5 to 10 μm, and the organic particles comprise polystyrene.

13. The method of claim 1, wherein the complex and the dissociation agent are combined at a temperature of from 20 to 40° C. and at a pH of from 5 to 9.

14. The method of claim 6, wherein the water-soluble polymer comprises bovine serum albumin, human serum albumin, or both, as a water-soluble protein.

15. The method of claim 1, wherein the dissociation efficiency is 70-96%.

* * * * *